United States Patent [19]
Hughes

[11] 3,936,674
[45] Feb. 3, 1976

[54] RATE SIGNAL GENERATOR CIRCUIT
[75] Inventor: Philip A. Hughes, Littleton, Colo.
[73] Assignee: Sandoz, Inc., E. Hanover, N.J.
[22] Filed: Mar. 5, 1974
[21] Appl. No.: 448,293

[52] U.S. Cl. ................. 307/233 R; 307/271; 320/1; 328/140
[51] Int. Cl.² ...................... H03K 1/16; H03B 3/04
[58] Field of Search ........... 330/18; 307/271, 233 C, 307/246 C, 235 C; 340/173 CA; 320/1; 328/140 C

[56] References Cited
UNITED STATES PATENTS
3,740,586  6/1973  Banks et al. ..................... 307/271 X Primary Examiner—Alfred L. Brody
Attorney, Agent, or Firm—Gerald D. Sharkin; Robert S. Honor; Walter F. Jewell

[57] ABSTRACT

Disclosed herein is circuitry for producing a signal proportional to the rate of recurrence of a periodic input signal applied to the circuitry. When an input pulse is received a timing circuit is energized to charge a capacitor to a predetermined level. The capacitor is then discharged through a resistance circuit having resistance portions which are electronically switched in and out of the circuit so that the discharge, rate of the capacitor defines the desired rate function. Then, upon commencement of a subsequent pulse a sample and hold circuit is actuated to sample the discharge level of the capacitor to provide an accurate indication of the pulse rate.

3 Claims, 1 Drawing Figure

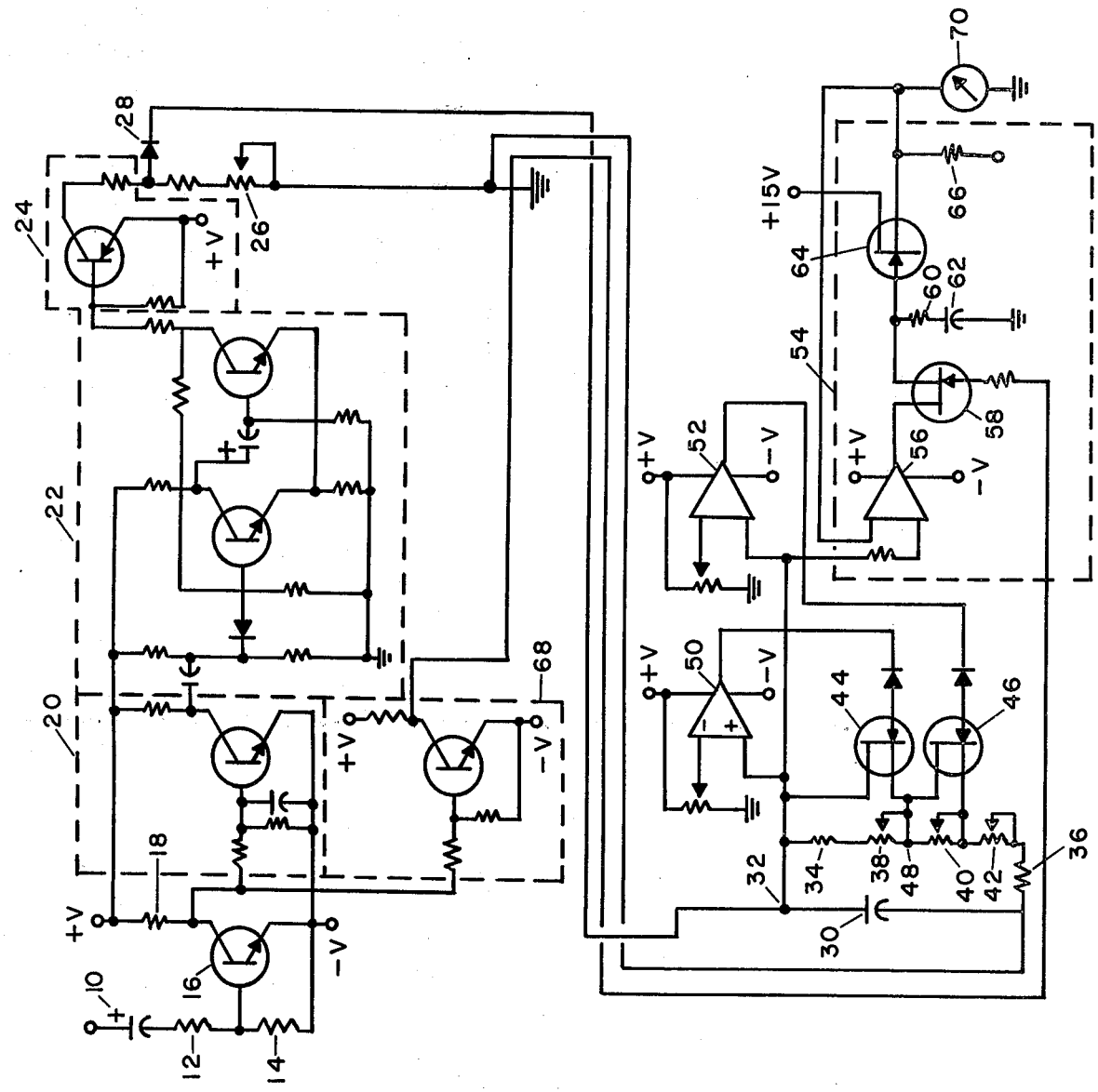

RATE SIGNAL GENERATOR CIRCUIT

BACKGROUND OF THE INVENTION

Prior to the instant invention it was known that a rate meter could be provided, for example, by arranging a plurality of capacitors to be charged to different voltage levels, and by connecting the capacitors through diodes to a discharge resistor, so that the discharge voltage across the resistor decreased in a manner defining a rate function due to the sequential connection of the respective capacitors into the discharge circuit as the diodes were in turn biased into conductive states by decreasing voltage. However, various drawbacks exist with respect to such prior art circuits in that the required plurality of capacitors have different tolerances, and the required diodes for switching the capacitors into the discharge circuit must have matched switching points. Accordingly, it is an object of the present invention to provide a rate meter circuit having improved accuracy and reliability characteristics with respect to the prior art.

SUMMARY OF THE INVENTION

In accordance with the invention there is provided a circuit for sensing the leading edges of recurring pulses, and for using each of those sensed signals to actuate a charging circuit for charging a capacitor to a predetermined level, during a predetermined time interval, whereupon the capacitor is then discharged through a series circuit formed by a plurality of resistors. The rate of recurrence of the input pulses is determined by sensing the discharge voltage of the capacitor upon initiation of the next succeeding input pulse, since the capacitor voltage will then be related to the period between such input pulses. To accomplish this function the preferred embodiment of the invention includes a sample and hold circuit, connected for actuation by the sensed impulses, and coupled to the capacitor to receive its sample voltage therefrom.

However, the discharge rate of the capacitor connected in an RC circuit defines the function $e^{-t/T}$, so that in the circuit described above some type of decoding step is necessary in order to convert the non-linear discharge voltage from the capacitor to a value which would give the function $1/t$, corresponding to the rate of recurrence of the input signal where $t$ is the time duration for one period of the recurring signal. In the present invention the necessity of performing such a decoding step is precluded by an electronic switching circuit connected to the plurality of series connected resistors in the discharge path in order to alter the resistance of that discharge path during the discharge of the capacitor, so that the characteristics of the discharging voltage across the capacitor is modified to provide the function $1/t$.

The electronic switching circuit accomplishes its desired result by adding one or more break points in the capacitor discharge curve, so that its discharge rate slows down. The number of such break points needed is determined by the accuracy required and the desired dynamic range of the circuit. In the preferred embodiment of the invention these break points are added by switching additional resistors into the discharge path of the capacitor.

In a specific embodiment of the invention there are five series connected resistors defining the discharge path for the capacitor, and a first switch is connected in parallel with the first two of such resistors, while a second FET switch is connected in series with the first such switch and in parallel with the third one of such resistors in the series connected path. The gate electrodes of the first and second FET switches are connected to respective threshold detectors, each having a first input to receive the charged voltage of the capacitor, and each having a second input connected respectively to different bias sources, so that when the full predetermined charge is present on the capacitor, both of the threshhold detectors provide positive outputs for biasing the first and second FET switches into their conductive states. Then, as the capacitor discharges to the sequential threshold levels, the detectors sequentially cut off the switches, so that the entire resistance circuit is eventually coupled into the discharge path. Accordingly, at the start of the discharge period for the capacitor, three of the resistors in the series connected discharge path are shorted by the FET switches so that the RC time constant for discharging the capacitor is at a relatively low level. Then, as the voltage across the capacitor decreases one of the threshold detectors is caused to switch its output to a negative signal thereby cutting off the first FET switch so that an additional pair of resistors is switched into the series connected discharge path. This increases the RC time constant thereby modifying the original discharge characteristic of the capacitor circuit; and, upon further discharge of that capacitor voltage the second threshold detector produces a negative output signal which cuts off the second FET switch thereby effectively inserting the remaining resistor into the discharge path, and again increasing the RC time constant to further modify the discharge characteristic of the capacitor.

BRIEF DESCRIPTION OF THE DRAWING

The accompanying drawing illustrates, in schematic form, a preferred embodiment of a rate meter according to the instant invention.

DETAILED DESCRIPTION OF A PREFERRED EMBODIMENT

In a preferred embodiment of the invention, as illustrated in the drawing, a periodic signal such as a pulse train is connected to a differentiator circuit comprising a capacitor 10 and a pair of resistors 12 and 14, wherein the capacitor 10 and the resistor 12 are connected in series to the base electrode of a transistor 16, while the resistor 14 is connected across the base emitter junction of that transistor. The transistor 16 serves as an amplifier and has a collector resistor 18 connected to a source of positive voltage, while the emitter of the transistor 16 is connected to a source of negative voltage. The output of the amplifier, taken at the collector of transistor 16, is applied through an inverter circuit 20 to a one-shot multivibrator 22 which generates a signal for a predetermined length of time commencing with the leading edge of the input signal applied to the differentiator capacitor 10.

The output from the multivibrator 22 is applied to an amplifier 24 which applies a charging current to an RC circuit comprising an adjustable resistor 26 connected in parallel with a diode 28 and a capacitor 30. Since the multivibrator 22 and amplifier 24 provide a charging signal at a known voltage for a known period of time, the capacitor 30 can be charged to any desired voltage by manipulation of the adjustable resistor 26. At the completion of the output signal generated by the one-shot multivibrator 22, the charging circuit is cut off from the capacitor by the diode 28, so that the amplifier 24 and adjustable resistor 26 have no effect on the discharge of the capacitor 30, whereby such discharge depends solely on the characteristics of an output circuit connected to the junction 32 between the capacitor 30 and the diode 28.

One portion of the output circuit connected to the junction 32 is defined by five resistors connected in series between that output junction and ground, wherein the first and fifth resistors 34 and 36 are fixed resistors and the remaining three resistors 38, 40 and 42 in the series circuit are adjustable.

In order to modify the discharge characteristic if the RC circuit to provide a rate function, a pair of FET switches 44 and 46 have their principal conducting electrodes connected in series between the output point 32 from the capacitor 30 and the junction of the third and fourth resistors 40 and 42. Also, the junction 48 between the two switches 44 and 46 is connected to the junction between the resistors 38 and 40, whereby it is seen from the drawing that the switch 44 is connected in parallel with the resistors 34 and 38, while the switch 46 is connected in parallel with the resistor 40. The gates of the FET switches 44 and 46 are connected to the respective outputs of a pair of threshold detector circuits 50 and 52 each having their positive input terminals connected to the output point 32 from the capacitor 30, and having negative bias inputs connected to respective adjustable positive potential sources.

In operation, both of the threshold detectors 50 and 52 provide a positive output when the voltage across the capacitor 30 is at a maximum value so that the resistance portion of the RC time constant is defined solely by the resistors 36 and 42 at the beginning of the discharge cycle of the capacitor 30. The voltages at the negative inputs to the threshold detectors 50 and 52 are arranged so that the detector 50 switches and its output to a negative value in response to a decreasing voltage across the capacitor 30 prior to a corresponding charge in output voltage of the detector 52. Thus, as the voltage across the capacitor decreases the device 44 switches to its non-conductive state thereby inserting the resistors 34 and 38 into the RC discharge circuit. Subsequently, as the voltage across the capacitor 30 decreases further, the threshold detector 52 provides a negative output which cuts off the FET switch 46 so that the entire series resistance circuit 34–42 is connected into the discharge path. It will be appreciated that the proper adjustment of the resistors 38, 40 and 42, as well as the proper adjustment of the voltages applied to the negative inputs of the threshold detectors 50 and 52, will result in a discharge characteristic for the capacitor 30 which defines an accurate rate function.

The modified discharge voltage characteristic of the capacitor 30 is applied to a sample and hold circuit 54 including a buffer amplifier 56; a sampling switch 58 connected in series between the output of the buffer amplifier 56 and a series connected resistor 60 and capacitor 62; and, an FET output transistor 64 connected to a load resistor 66. The gate electrode of the sampling switch 58 is connected for actuation to the output of an amplifier 68 having its input in turn connected to the output of the amplifier transistor 16 which detects the leading edge of the differentiated input signals applied to the capacitor 10. Sample and hold circuit 54 operates to sample the voltage across the capacitor 30 at the commencement of each input signal applied to the input capacitor 10, so that it can be seen that the output device 64 provides an output voltage which is updated at the time of each input pulse to define the recurrence rate of the pulses. This result is attainable since the voltage on the capacitor 30, which is sampled by the circuit 54, is directly proportional in magnitude to the rate of input pulses applied to the circuit, and can be applied to a voltmeter mechanism to give a direct reading of the rate.

Among other applications, the rate meter circuit described herein is particularly adaptable for combination with a respiratory test device which produces output information related to the breathing characteristics of a patient. For example, the input signals can be derived from a detector such as a bellows switch for sensing successive exhalations of a patient, so that the rate signal generated by the circuit will indicate the patients breathing rate. Thus, the capacitor voltage (R) which is sampled and held will satisfy the equation $R = 1/t$, where the voltage R indicates the patient's breaths per minute and the value $t$ is the time, in minutes, for each breath.

Also, it is to be understood that the circuit for altering the discharge rate of a capacitor, as disclosed herein, can be modified to change that discharge rate to conform to a multitude of different types of curves depending upon whether the FET switches connected in parallel with the discharge resistors are switched into or out of conduction as as the voltage across the capacitor decreases. For example, in the circuit illustrated in the schematic drawing hereof, the FET switches can be connected to change from nonconductive to conductive states as the capacitor discharges, so that the resultant discharge curve will be linearized.

I claim:

1. A rate signal generating circuit for determining the rate of recurrence of electrical signals, said circuit comprising means for sensing said electrical signals, a capacitor, charging circuit means connected between said sensing means and said capacitor to charge said capacitor to a predetermined voltage level during a predetermined time interval in response to the sensing of one of said electrical signals, a plurality of resistors connected in series and coupled to said capacitor to provide a discharge path therefor, electronic switch means connected to said resistors and said capacitor for shorting selected said resistors in response to predetermined charged voltages across said capacitor, wherein said capacitor discharges to define a rate function, and sample and hold means coupled to said capacitor and said sensing means for actuation by each successive said electrical signal to provide an output voltage proportional to the rate of recurrence of said signals.

2. A rate signal generator as set forth in claim 1 wherein said plurality of resistors connected in series comprises at least three resistors, and wherein said electronic switch means comprises first and second FET switches connected in parallel with respective ones of said three resistors, said FET switches having gate electrodes, said electronic switch means further including first and second threshold detector means, each having first inputs connected to said capacitor, and having second inputs for connection to respective different sources of bias voltages, said threshold detector means each having outputs connected respectively to said gate electrodes of said FET switches, wherein said first and second threshold detector means are energized sequentially by a discharging voltage across said capacitor to sequentially actuate said FET switches, thereby altering the said discharge resistance path connected to said capacitor.

3. A rate signal generator circuit as set forth in claim 2 wherein said sample and hold means comprises a buffer amplifier having an output, and having an input coupled to said capacitor, an FET sample switch, a signal storing capacitor connected through said FET sample switch to the output of said buffer amplifier, said FET sample switch having a gate electrode connected for control to said sensing means, and an FET output transistor connected to said signal storing capacitor to provide said output voltage proportional to the rate of recurrence of said signals.

* * * * *